United States Patent [19]

Barnickel et al.

[11] 4,073,838
[45] Feb. 14, 1978

[54] GRANULATING PROCESS

[75] Inventors: Heinrich Barnickel; Winfrid Sigl; Jorg Schwable, all of Biberach an der Riss, Germany

[73] Assignee: Boehringer Ingelheim GmbH, Ingelheim am Rhein, Germany

[21] Appl. No.: 688,104

[22] Filed: May 19, 1976

Related U.S. Application Data

[63] Continuation-in-part of Ser. No. 496,864, Aug. 12, 1974, abandoned.

[51] Int. Cl.² ............................................... B01J 2/16
[52] U.S. Cl. ...................................... 264/37; 264/117
[58] Field of Search ............... 264/117, 118, DIG. 51, 264/37

[56] References Cited

U.S. PATENT DOCUMENTS

| | | | |
|---|---|---|---|
| 2,938,233 | 5/1960 | Nack et al. | 264/7 |
| 3,880,968 | 4/1975 | Kaspar et al. | 264/117 |

*Primary Examiner*—Robert F. White
*Assistant Examiner*—James R. Hall
*Attorney, Agent, or Firm*—Hammond & Littell

[57] ABSTRACT

A batch process for forming a granulate of predetermined granule size distribution from a powdered solid substance or, a mixture of powdered solid substances, which comprises the steps of (a) blowing hot air upwardly through a batch of said mixture of powdered substances to form a fluidized bed having a lower portion and an upper portion, (b) spraying into the upper portion of said fluidized bed a hot bonding liquid at a rate sufficient to cause the particles of the powdered substances to coalesce and initiate a buildup of granules, (c) simultaneously breaking down the built-up granules in the lower portion of the fluidized bed by impact with rigid blades moving at high speed to establish an equilibrium between build-up and break-down of granules, the granule build-up rate slightly exceeding the break-down rate, and (d) recovering the granulate when the desired granule size distribution has been achieved.

4 Claims, 1 Drawing Figure

U.S. Patent     Feb. 14, 1978     4,073,838
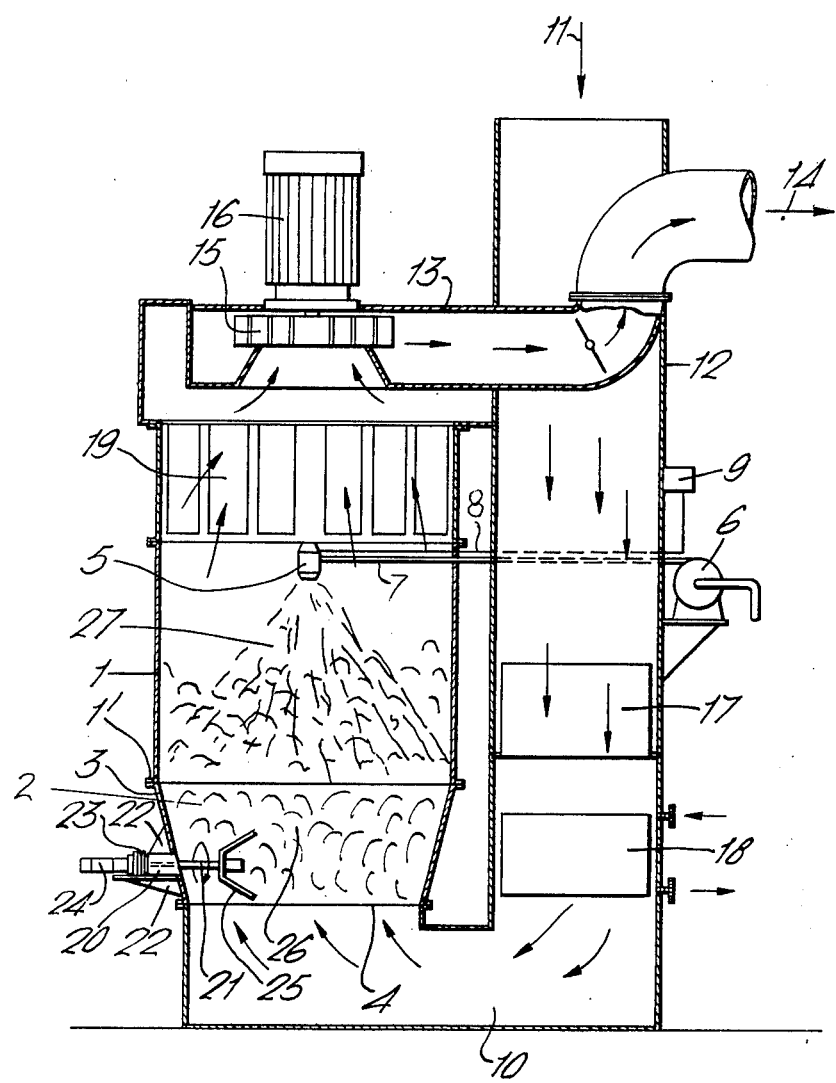

GRANULATING PROCESS

This is a continuation-in-part of copending application Ser. No. 496,864 filed Aug. 12, 1974, now abandoned.

This invention relates to a novel granulating process by the fluidized bed method.

BACKGROUND OF THE INVENTION

It is known that pharmaceutical preparations can be produced as uniform granules from a mixture of powdered ingredients, which powdered ingredients are of different particle size, bulk density, and specific weight and are present in differing proportions. The powdered ingredients are placed into a closed container having a perforated base through which heated air is driven by a fan from below the base. This air flow is so regulated in relation to the container and the powdered mixture therein that the powder particles are upheld or suspended in what is known as a fluidized bed. A thorough mixing of the individual powder particles takes place in the fluidized bed. Subsequently, or simultaneously, there is sprayed into the fluidized bed, by means of a nozzle a liquid which usually contains a binder. Powder components are dissolved by the liquid, so that subsequently they can act as binding agents. When drops of liquid are combined with powder particles, the particles are able to adhere to other powder particles by means of liquid bonds. The liquid evaporates as a consequence of the high air through-put, and bonds of solid material are formed between the powder particles, by crystallization of the substances dissolved within the liquid or by hardening of the binders.

In contrast to other known granulating techniques, wherein the granules are formed by the pulverization of relatively large agglomerates, the granulate formation in the above-described fluidized bed spray granulating process occurs by a continuous enlargement of the original powder particles.

In the above-described fluidized bed spray granulating process, the more moist the mass of powder materials is maintained during the spraying phase, that is, the faster the granulating liquid is sprayed in, the more rapidly the size of the individual granules (among other things) is increased. For economy reasons, it is desirable to reduce the spray time by spraying the liquid more quickly. However, if the spray time is reduced too greatly, agglomerates the size of snowballs are formed. These agglomerates only dry on their outer surfaces during the subsequent drying phase, whereas in their interior they remain moist, so that the mass as a whole is non-uniformly dried. If the spraying time is reduced even further, the entire mass forms a damp cohesive cake on the perforated base, into which the airflow penetrates through cracks and channels. However, this damp cohesive cake can no longer be lifted up by the airflow alone and no longer forms a fluidized bed. Therefore, the speed in the fluidized bed spray granulating process, is correspondingly limited in each case according to the quality of the granulate.

DESCRIPTION OF THE INVENTION

The present invention relates to a method for granulating a powdered substance or a mixture of powdered substances in a fluidized bed.

The above-mentioned disadvantages of the prior art fluidized bed spray granulating processes are overcome, or at least reduced by means of the process according to the present invention which provides for a controlled breakdown of the built-up granules during the spraying phase and thus prevents the formation of large agglomerates.

More particularly, the present invention relates to a batch process for forming a granulate of predetermined granule size distribution from a powdered solid substance or a mixture of powdered solid substances, which comprises the steps of
 (a) blowing hot air upwardly through a batch of said powdered substance or said mixture of powdered substances to form a fluidized bed having a lower portion and an upper portion,
 (b) spraying into the upper portion of said fluidized bed a hot bonding liquid at a rate sufficient to cause the particles of the powdered substances to coalesce and initiate a buildup of granules,
 (c) simultaneously breaking down the built-up granules in the lower portion of the fluidized bed by impact with rigid blades moving at high speed to establish an equilibrium between build-up and break-down of granules, the granule build-up rate slightly exceeding the break-down rate, and
 (d) recovering the granulate when the desired granule size distribution has been achieved.

Thus, in accordance with the present invention, a controlled breakdown of the granulate is performed. As was mentioned above, the known fluidized bed spray granulating technique consists in a continuous enlargement of the granules. In accordance with the present invention, this continuous enlargement is prevented by breaking-up or crushing means. It is thus possible for the quantity of liquid sprayed per unit time to be substantially increased, as compared with the known method, without this leading to the formation of large agglomerates with an irregular moisture distribution, or to the entire mass becoming stuck together. In this manner, the entire granulating time, inclusive of the drying phase, can be shortened by 30 to 70%. The granulates thus produced possess technological and galenic properties which are as good as, or better than those of granulates prepared according to the prior art.

The success of the method according to the instant invention is surprising in view of known factors which suggested that the present invention was not practicable, and which are as follows: It is known that a fluidized bed is considerably disturbed by the incorporation of obstacles into the fluidized bed. Under certain circumstances it is possible for a screening action to occur to such a great extent that the desired turbulence in the bed almost completely ceases within large areas. This effect might be thought to be considerably reinforced by the inclusion of break-up means which, during its operation in the fluidized bed, produces a zone of lower density so that the airflow preferably passes in and through this zone, whereas in other zones the damp constituents are subjected to turbulence of lesser strength. In this manner, it would be possible for holes in the bed to form gradually around the break-up means through which the airflow penetrates preferentially without any turbulence, whereas at other places the moist granulate masses are completely deposited. The controlled breakdown of the granulate is in complete contradiction to the heretofore accepted principles of fluidized bed spray granulating processes. It was, therefore, completely surprising that we found that the above considerations did not apply, and that it was possible to establish an equilibrium between the break-up and the build-up of the granulate. This equilibrium can be controlled in a simple and completely satisfactory manner.

According to the fluidized bed spray granulating process in accordance with the invention, in contrast to the fluidized bed spray granulating process heretofore known in the prior art, whose method of operating consists in a continuous agglomeration or granule build-up, the granulate formed is partially broken down so that an equilibrium is produced between the granule build-up and granule break-up. This equilibrium can be very easily influenced, for example, by controlling the fluidized bed, by controlling the temperature of the air forming the fluidized bed, by controlling the liquid spray rate and/or by controlling the action of the break-up means. It is thus possible to control the granulate size by varying the above-mentioned parameters.

In contrast to the prior art pulverization granulating techniques, in the process according to the invention all of the advantages of the fluidized bed spray granulating technique are retained, such as operating in a closed system, faster operation and elimination of intermediary work steps, or even improved. Moreover, several advantages arise which at first were not foreseen.

It is known that in conjunction with mixtures of powdered substances with very different bulk volumes, such as often occur in the constituents used for granulating processes, difficulties arise in the fluidized bed spray granulating thereof, because, with slow spraying, as is used in known processes, there is a sufficient residence time for a wind sifting to occur. That is, a dissociation takes place before the powder mixture is moistened with the granulating liquid. In the process in accordance with the present invention, this effect need not occur for practical purposes, because the entire bonding liquid can be sprayed in within a very short time.

It is further known that substances which easily become electrostatically charged (these are sometimes required to be granulated) can only be granulated under extreme conditions, or not at all, in a fluidized bed spray granulator. This is because these substances very rapidly become deposited on the container wall and/or dry up so that pigeon's egg-sized balls of powder are formed, which fall again as dust during the subsequent drying phase or during the screening step which then becomes necessary. This disadvantage also can be almost completely prevented by very rapid moistening with the bonding liquid and by breaking up of the balls according to the invention.

According to the process of the invention it is possible to succeed in producing granulates in the fluidized bed spray granulator which could not be prepared in accordance with the heretofore known methods of the prior art.

While the break-up means may be any suitable device, it preferably consists of rapidly moving mechanical means. It could, for example, consist of a reciprocatory member, solid or perforated, rapidly reciprocating across the length or breadth of the lower portion of the fluidized bed.

As a preferred embodiment, the break-up means consists of a plurality of rigid blades mounted on one or more shafts. We have found that a plurality of blades mounted on a single shaft is sufficient, with the blades preferably being located in or adjacent to the lower portion of the fluidized bed, or at least spaced from the side and corners of the fluidized bed container. While the shaft may be mounted in any suitable manner, it is convenient for the shaft to be mounted in a side wall of the container. The blades may be perpendicular to the shaft, but we have found that a better break-up action is achieved if the main parts of the blades are inclined at a substantial angle to the shaft. The blades are preferably arranged at such a height above the container base that they are entirely within the fluidized bed in operation and in the rest condition are completely covered by the initially powdered mixture. The blades are preferably located adjacent the container base, so that their action in use is initiated at the base.

A preferred embodiment of the apparatus for carrying out the method of the instant invention will now be described with reference to the accompanying drawing, which is a schematic sectional view of one embodiment of apparatus. The drawing is not to be deemed limitative in any manner.

The apparatus includes a vertical cylindrical spray housing 1 sealingly but releasably secured at its base 1' to a container 2 for receiving the mixture of powdered substances from which the granulate is to be manufactured. Container 2 is annular and has inwardly sloping sidewalls 3 terminating a circular perforated base 4 made of stainless steel wire mesh. The mesh size is selected so that the mixture of powdered substances placed into the container cannot pass through the mesh.

At the top of spray housing 1 is mounted a downwardly directed spray nozzle 5. Nozzle 5 is supplied in operation with bonding liquid (which may be organic or inorganic and usually contains a binder, such as gelatin, starch or polyvinylpyrrolidone) from a reservoir (now shown) by a pump 6 forcing the liquid through a conduit 7 to the nozzle 5. The nozzle 5 is also supplied with compressed air by a conduit 8 from a compressed air source 9.

The containers 1 and 2 form part of an air passage 10 which extends from an air inlet 11, through a vertical pipe 12 which communicates with the base 4 of container 2, through containers 1 and 2 and thereafter through a pipe 13 to an air exhaust 14. A fan 15 drivingly connected to a motor 16 is provided above containers 1 and 2 for driving air through the air passage 10. As the air passes down pipe 12 it is filtered by an air filter 17 and heated by an air heater 18 (both filter and heater are of conventional construction and are indicated symbolically). A further filter 19 with an annular manifold is provided directly above housing 1.

Fixedly mounted in container sidewall 3 is a bearing 20 for a rotary shaft 21 extending radially inwardly of container 2. Bearing 20 has supports 22. Shaft 21 is connected through a clutch 23 to a drive shaft 24 which is in turn connected to a motor (not shown) for rotating the shaft at speeds of from at least 1000 up to 4000 rpm.

A pair of blades 25 shown in section are mounted adjacent the free end of shaft 21 on opposite sides of the shaft. The blades have portions perpendicular to shaft 21 in the regions of their connection to shaft 21, but the major operative parts of the blades are inclined at an angle of about 30° to the shaft. The blades 25 extend radially of the container roughly halfway between the side wall 3 and the center of the container 2 and have a radial extent of about one-third the radius of the container 2. Blades 25 are mounted so that they pass, as shown, in the drawing, very close the base of the container and extend up to about two-thirds of the height of the container whereby they are completely covered by the mixture of powdered substances placed into container 2.

The mixture of powdered substances from which the granulate is to be manufactured are placed into container 2 so that it covers blades 25. Container 2 is then positioned under and secured to container 1. Fan 15 is started up, and air is drawn into air inlet 11 into pipe 12. The air is filtered in filter 17 and heated to the required temperature in heater 18. The air then passes through container base 4 and lifts the constituents in the container to form a fluidized bed, indicated schematically at 26. The air passes out through filter 19 which filters out and prevents powder particles from being lost through air exhaust 14.

Blades 25 are rotated at a desired speed. When the fluidized bed is at the desired temperature, compressed air from source 9 and bonding liquid via pump 6 are supplied to spray nozzle 6.

The spray is directed onto the fluidized bed and forms a cone indicated at 27 which strikes the sidewalls of housing 1 approximately at the base of housing 1. The bonding liquid reacts with the powder particles in known manner to coalesce the particles to form granules by continuous enlargement. Blades 25 are meanwhile rotating and drawing the granules into the turbulent region created by their rotation. The granules, or at least the largest granules, are broken down in this region into smaller granules and the formation of large agglomerations is prevented. After the desired granule size distribution has been achieved, the blades are turned off, and after a further period of drying, if necessary, in the fluidized bed, the granulate is extracted from the container 2 by releasing container 2 from housing 1 and moving the container 2 to an extraction station.

To illustrate the advantages in the speed of the process, a specific example will now be given, which is not to be deemed limitative of the present invention in any manner thereof.

EXAMPLE

A mixture of powdered substances consisting of 130 kg of lactose and 11.4 kg of colloidal silicic acid was charged into container 2 and this was then placed beneath the spray container 1. By regulating the speed of the fan 15 the air flow was so controlled that with an air throughput of 2,500 cubic meters per hour, the powder particles were maintained in a fluidized bed so that mixing was effected. The bonding liquid, a solution of 5 kg of gelatin and 1.2 kg of glycerin in 40 liters of water, was at the same time sprayed onto the fluidized bed at a liquid temperature of 70° C and at a rate, produced by the pump 6, of 10 liters per minute and at a spray pressure of 3.5 atmospheres produced by the compressed air source 9. The air temperature was determined by heater 18 for the spraying phase at 70° C and for the drying phase at 100° C; that is, when the spraying phase was completed the heater made the air hotter. The blades 25 were started at the same time as the bonding liquid spray; the running time was 15 minutes and the speed of the blades was 1,800 r.p.m. At the end of this time an equilibrium between build-up and break-up of granules was established, the granule build-up rate slightly exceeding the break-up rate. The blades were now turned off, but hot air drying continued until the granulate had a moisture content of 1.5%. Thereafter, screening took place at an extraction station by means of a 1.5 mm-mesh screen. The finished granulate had a granule size distribution as follows: 5% below 0.1 mm., 13% between 0.1 and 0.16 mm., 33% between 0.16 and 0.25 mm., 22% between 0.25 and 0.5 mm., 12% between 0.5 and 0.8 mm., 5% between 0.8 and 1 mm. and 10% between 1 and 1.6 mm. The volume of the granulate amounted to 168 ml/100 gm.

In the present example the saving of time was 44% compared with the conventional fluidized bed spray granulating procedure.

Various modifications may be envisaged to the above described embodiment without departing from the scope of the invention claimed. For example, a plurality of shafts with associated crushing blades may be disposed around the perimeter of the powder container. Each shaft may have a set of blades of any number (symmetrically disposed about the shaft for balance) and may have more than one set of blades with each set being axially spaced along the shaft from other sets. While for convenience, the shaft or shafts are mounted in the fluidized bed container they could be mounted elsewhere, for example, in the spray housing and extend into the container.

The granulating process of the present invention is particularly useful for the preparation of granulates in the pharmaceutical industry, that is, granulates which are subsequently compressed in conventional manner into pharmaceutical tablets or pill cores; however, the process is equally applicable to other fields, such as in the manufacture of granulated chemical compositions, alimentary compositions for human consumption, and animal feedstuff compositions.

We claim:

1. A batch process for forming a product granulate having a predetermined granule size distribution from a powdered starting material selected from the group consisting of a single powdered solid substance or a mixture of powdered solid substances, the particles of the granulated product being larger than the particles of the powdered starting material, which comprises the steps of
   (a) blowing air at an elevated temperature upwardly through a batch of said powdered starting material to form a fluidized bed having a lower portion and an upper portion,
   (b) spraying into the upper portion of said fluidized bed a bonding agent solution at a rate sufficient to cause particles of powdered starting material in the upper portion of the fluidized bed to coalesce and build-up granules, whereupon large granules migrate from the upper portion to the lower portion of the fluidized bed,
   (c) breaking up large granules in the lower portion of the fluidized bed into smaller granules by impact with rigid blades moving at high speed such that the build-up of granules in the upper portion of the fluidized bed slightly exceeds the break-up of granules and until the desired granule size distribution is achieved,
   (d) stopping the bonding agent spray, the blade motion and the air blowing, and
   (e) recovering the product granulate.

2. The process of claim 1, wherein said built-up granules are broken up by impact with rigid blades oscillating at high speed.

3. The process of claim 1, wherein said built-up granules are broken up by impact with rigid blades rotating at high speed.

4. The process of claim 3, where said blades rotate at a speed of 1,000 to 4,000 r.p.m.